United States Patent [19]

Gandrud

[11] Patent Number: 5,027,138

[45] Date of Patent: Jun. 25, 1991

[54] DENTAL CAMERA SYSTEM

[76] Inventor: S. Garfield Gandrud, 414 Baywood Dr., Newport Beach, Calif. 92660

[21] Appl. No.: 557,161

[22] Filed: Jul. 23, 1990

[51] Int. Cl.$^5$ ............................................. A61B 1/04
[52] U.S. Cl. ........................................ 354/62; 358/98
[58] Field of Search ............... 354/62; 358/98; 433/31

[56] References Cited

U.S. PATENT DOCUMENTS 4,915,626 4/1990 Lemmey ........................... 358/98 X Primary Examiner—Michael L. Gellner
Attorney, Agent, or Firm—Roy A. Ekstrand

[57] ABSTRACT

A dental camera system includes an elongated cylindrical housing having an internal cavity for supporting a miniature video camera. The housing includes an elongated notch which exposes the focusing and aperture adjustment controls of the video camera for easy manipulation. An elongated knurled focusing sleeve is coupled to the focus ring of the camera. The housing further supports a pair of fiber-optic light pipes having offset positioning with respect to the camera lens to provide an improved illumination pattern. A dental mirror is coupled to an extendable support within the housing and a multiply positioned detent mechanism permits the mirror extension from the camera lens to be adjusted. The housing terminates at the end remote from the camera lens in a pair of opposed C-shaped split caps which provide closure of the housing end and encircle the camera cable and light pipes.

13 Claims, 2 Drawing Sheets

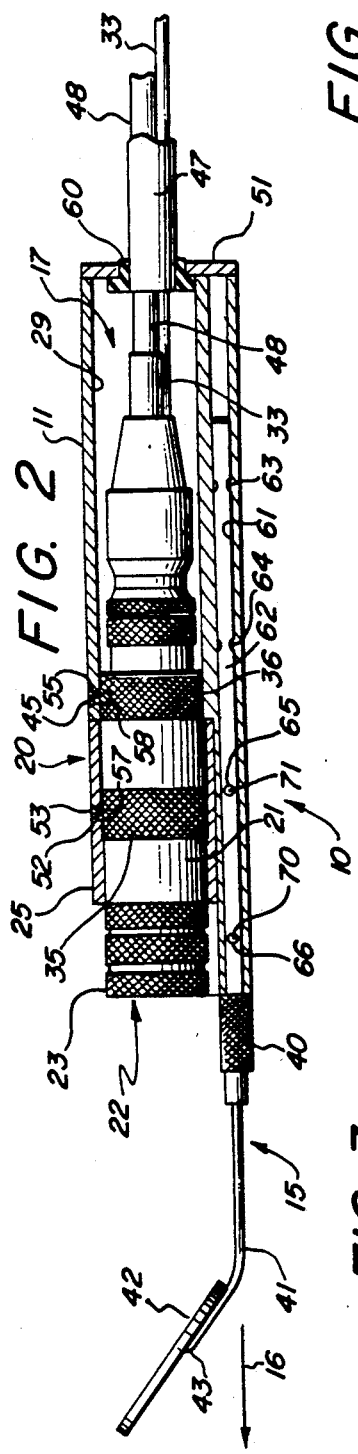
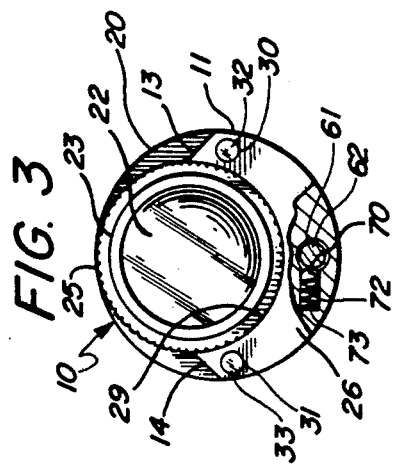
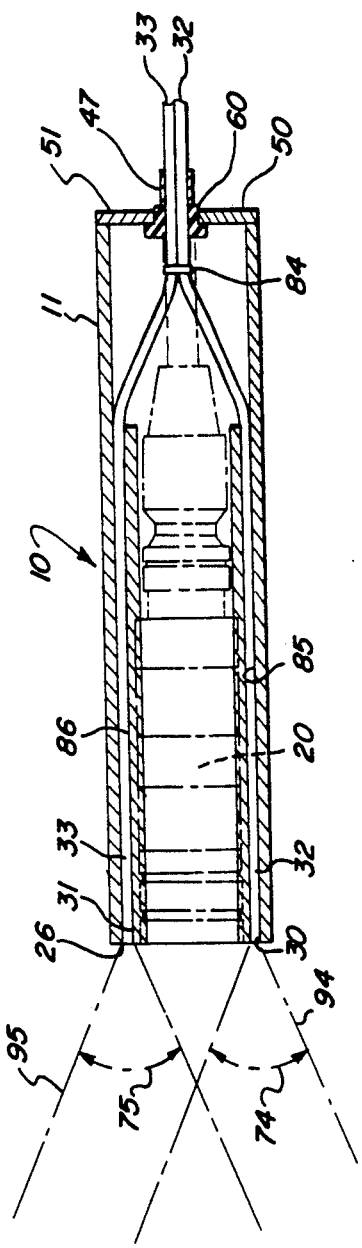

DENTAL CAMERA SYSTEM

FIELD OF THE INVENTION

This invention relates generally to dental imaging systems and particularly to those utilizing miniature video cameras.

BACKGROUND OF THE INVENTION

For many years, practitioners of dentistry and related arts were severely limited in their ability to visually examine the teeth and oral cavity of their patients. The most prevalent system involved the use of direct illumination sources and a variety of specially configured mirrors and mirror supports. With the development of miniaturized video cameras, the examining systems available to dental practitioners received a significant improved and enhanced capability. Such video cameras were quickly utilized in a variety of video systems which, while assuming a variety of configurations, generally included a miniature video camera coupled to a convenient video display such as a monitor or conventional television receiver. In most instances, a video recorder is combined with the video display to preserve a visual record of the examination. Often an auxiliary light source is supported near the miniature video camera to provide intraoral illumination and improve examination capability.

While several miniature video cameras have been constructed, one of the more popular of such video cameras is that manufactured by Elmo Company Limited having model numbers EM102 and EM102BW. The desire to provide video imaging system for use in dental examination has prompted practitioners in the art to provide a variety of imaging systems utilizing such miniature video cameras.

One such example of the presently available dental imaging systems is marketed by Lester A. Dine, Inc. under the trademark Oral Scan which utilizes an elongated cylindrical housing to support a miniature video camera of the type referred to above. An outwardly extending pistol grip type handle is secured to the cylindrical housing and is positionally adjustable. A support bracket secured to the cylindrical housing and the pistol grip handle supports a conventional dental examination mirror. In addition, the support bracket further supports a fiber-optic illumination source beneath the cylindrical housing and camera.

Another presently available device is manufactured by New Image Industries, Inc. under the trademark Intraview in which an elongated cylindrical handle supports a miniature video camera of the type referred to above. An elongated generally conical shroud is secured to the frontal portion of the housing and extends beyond the video camera. The shroud defines a large aperture which supports a mirror aligned to reflect light to the video camera aperture and a smaller aperture which supports a fiber-optic illumination system.

Another presently available device is manufactured by Acuimage Corporation under the trademark Acucam in which a miniature video camera of the type referred to above is supported within an elongated cylindrical housing. A pair of fiber-optic light sources are positioned adjacent the camera lens to provide illumination and a clip-on mirror support is removably attachable to the cylindrical housing and supports an elongated beam having an angled mirror at the end portion thereof.

Another presently available device is manufactured by Dentsply International, Inc. under the trademark Dental Vision which utilizes a miniature video camera in combination with a high intensity xenon light source. The camera is housed within an elongated cylindrical housing having a generally cylindrical reduced diameter extending portion which terminates in a viewing aperture and xenon light source.

Another of the presently available dental imaging systems is manufactured by Fuji Optical Systems, Inc. under the trademark Dentacam. The Dentacam system utilizes an elongated cylindrical housing which completely encloses a miniature video camera. One end of the housing adjacent the camera lens includes an elongated optical coupling pipe terminating in a head portion which supports a lens system and illumination source. The head is angled with respect to the extension to aid in examination of certain portions of the patient's oral cavity.

While the above-described systems provide substantial improvement over direct unaided optical examination of dental patients, the structures thus far provided are generally expensive and often bulky and cumbersome to work with. In addition, substantial portions of the systems must be sterilized at considerable inconvenience. In addition, the systems thus far provided are often inconvenient to operate in that the focus and aperture setting of the camera frequently requires removal of the camera from the systems' housing. Also, the above systems are sometimes subject to poor illumination quality which in turn limits the quality of image available.

There remains, therefore, a continuing need in the art for evermore improved dental imaging systems.

SUMMARY OF THE INVENTION

Accordingly, it is a general object of the present invention to provide an improved dental camera system. It is a more particular object of the present invention to provide an improved dental camera system which is relatively inexpensive and convenient to use. It is a still more particular object of the present invention to provide an improved dental camera system which may be easily and conveniently sterilized between uses. It is a still more particular object of the present invention to provide an improved dental camera system which facilitates the manipulation and aperture adjustments of the miniature video camera.

In accordance with the present invention, there is provided for use in imaging a portion of the mouth and teeth of a patient, a dental camera system comprises: a video camera defining an elongated generally cylindrical shape and having a frontal lens, an aperture adjustment ring, a focus adjustment ring and a connecting cable; a housing defining a generally cylindrical shape and having an interior passage configured to receive the camera such that the aperture adjustment ring and focus adjustment ring are exposed; a pair of light sources positioned in an offset array adjacent the frontal lens; a mirror support coupled to the housing and adjustably extending thereupon; and a mirror secured to the mirror support.

BRIEF DESCRIPTION OF THE DRAWINGS

The features of the present invention, which are believed to be novel, are set forth with particularity in the appended claims. The invention, together with further objects and advantages thereof, may best be understood by reference to the following description taken in conjunction with the accompanying drawings, in the several figures of which like reference numerals identify like elements and in which:

FIG. 2 sets forth a section view of the present invention dental camera system taken along section lines 2—2 in FIG. 1;

FIG. 3 sets forth a partially sectioned front view of the present invention dental camera system;

FIG. 4 sets forth a rear view of the present invention dental camera system; and FIG. 5 sets forth a top section view of the present invention dental camera system taken along section lines 5—5 in FIG. 4.

DESCRIPTION OF THE PREFERRED EMBODIMENT

Figure 1:
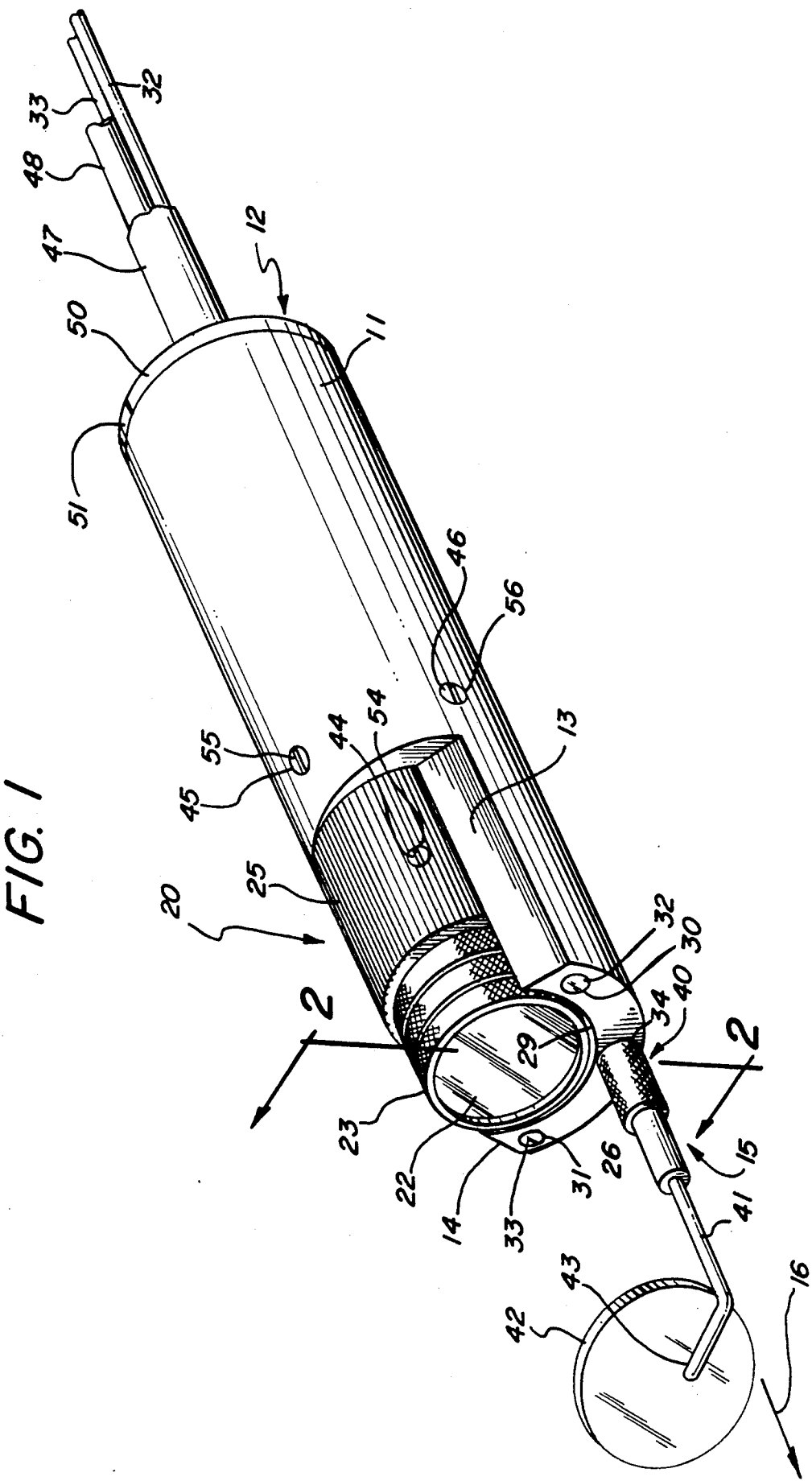
FIG. 1 sets forth a perspective view of a dental camera system constructed in accordance with the present invention.

FIG. 1 sets forth a perspective view of a dental camera system constructed in accordance with the present invention and generally referenced by numeral 10. Camera system 10 includes a generally cylindrical housing 11 defining a pair of inclined facets 13 and 14 extending rearwardly from a front face 26. Front face 26 defines a pair of apertures 30 and 31 and a cylindrical camera passage 29. Front face 26 further defines an aperture 34. A mirror support 15 includes a generally cylindrical threaded coupler 40 received within aperture 31 in the manner set forth below in greater detail. Threaded coupler 40 further supports a mirror shaft 41 and a mirror attachment 43. A conventional mirror 42 is secured to mirror shaft 41 at attachment 43. A pair of light pipes 32 and 33 are received within apertures 30 and 31 respectively and in their preferred form comprise a pair of fiber-optic light bundles. A miniature video camera 20 defines a generally cylindrical camera body 21 and is received within camera passage 29 of housing 11. Camera 20 is preferably constructed in accordance with a miniature video camera of the type manufactured by Elmo Company Limited model EM102 or EM102BW as described above. Camera 20 further includes a cylindrical lens ring 23 supporting a front lens 22. A cylindrical aperture 24 is movably secured upon camera body 21 and is operative to provide adjustment of the aperture setting for camera 20. A focus sleeve 25 is received upon camera 20 and, as described below in greater detail, is coupled to a focus adjusting ring 35 of camera 20. A cable sheath 47 extends from camera 20 and is coupled thereto in accordance with conventional fabrication techniques. Light pipes 32 and 33 are received within camera sheath 47 as set forth below. An end cap 12 comprises a pair of generally C-shaped split caps 50 and 51 secured to housing 11 as is better seen in FIG. 4.

In accordance with the invention, focus sleeve 25 defines a plurality of apertures such as aperture 54 which receive a corresponding plurality of set screws such as set screw 44 in a threaded attachment to secure focus sleeve 25 to focus ring 35 (seen in FIG. 2). Similarly, housing 11 defines a plurality of apertures such as apertures 55 and 56 which receive a plurality of set screws such as set screws 45 and 46 to secure housing 11 to collar 36 (seen in FIG. 2) of camera 20.

In operation, camera 20 is energized in accordance with conventional fabrication techniques to receive imaging light through lens 22 and to process the received imaging light and produce a corresponding imaging signal which is coupled to conventional circuitry for video display and other video processing in further accordance with conventional fabrication techniques. Because camera 20 is securely received and supported within camera passage 29 of housing 11, the manipulation of housing 11 provides a convenient mechanism for directing and utilizing camera 20 in accordance with dental imaging processes. During such imaging, aperture ring 24 is manipulated to provide aperture adjustment of camera 20. Similarly, focus sleeve 25 which, as mentioned, is secured to focus ring 35 of camera 20 may be rotated to provide focus adjustment for camera 20. In accordance with an important aspect of the present invention, housing 11 due to its small diameter cylindrical configuration provides a convenient secure housing for camera 20. In further accordance with the present invention, the elongated notch in housing 11 formed by facets 13 and 14 provides easy access to aperture ring 24 and focus sleeve 25. Accordingly, camera system 10 permits easy adjustment of aperture ring 24 and focus sleeve 25 without the need of removing camera 20 from housing 11.

Light pipes 32 and 33 are coupled to a source of illuminating light (not shown). The light coupled to light pipes 32 and 33 is directed outwardly through apertures 30 and 31 respectively to provide illumination sources for the to-be-imaged objects for dental camera system 10. Threaded coupler 40 and mirror support 15 cooperate to provide a convenient support for mirror 42. In accordance with an important aspect of the present invention described below in greater detail, mirror support 15 includes an elongated shaft received within housing 11 in a detented attachment also described below in greater detail. Suffice it to note here, however, that mirror support 15 may be supported proximate to lens 22 in the manner shown in FIG. 1 or may alternatively be withdrawn partially from housing 11 in the direction indicated by arrow 16 to provide extension of mirror support 15 and increase the distance between mirror 42 and lens 22. In addition, threaded coupler 40 permits mirror shaft 41, attachment 43 and mirror 42 to be removed from the remainder of camera system 10 for conventional sterilization and interchangeable replacement. Thus, a number of alternative configuration mirror and mirror supports may be utilized in a cooperative attachment with threaded coupler 40.

As is described below in greater detail, end cap 12 comprises a pair of oppositely facing C-shaped split caps 50 and 51 which are secured to housing 11 by a plurality of threaded fasteners. Split caps 50 and 51 are received on either side of cable sheath and thus may be removed to permit camera 20 to be completely removed from housing 11 by removal of set screws 45 and 46 without the need of disturbing the connections to cable 48.

Thus, in use, camera system 10 may be conveniently used to provide imaging of the interior portions of a dental patient's oral cavity. In such use, mirror 42, light pipes 32 and 33 and camera 20 cooperate to image the selected areas of the patient's oral cavity. Additionally, mirror support 15 may be completely removed from housing 11 to permit direct imaging by camera 20. During both instances, the illuminating light provided by light pipes 32 and 33 provide offset overlapping sources of illumination which cooperate to avoid undesired shadows in the to-be-imaged objects. In accordance with a further advantage of the present invention structure, mirror support 15 may be removed and camera 20 may be withdrawn from the patient's oral cavity to provide an external full face or partial face imaging of the patient's mouth and oral cavity.

Thus, in accordance with an important aspect of the present invention, the cylindrical shape and compact construction of camera system 10 provides convenient ergonometric design for a natural fit within the dental practitioner's hands. The housing supports a camera having a body diameter of eleven sixteenths of an inch and yet has an overall diameter of one inch. In further accordance with the present invention, the location of facets of 13 and 14 provide ease of operation in that focus sleeve 25 and aperture ring 24 may be conveniently and easily adjusted. In addition, the open notch formed by facets 13 and 14 provide a convenient orientation reference to aid the practitioner in orienting the camera system. It should be noted that cable sheath 47 emerges in axial alignment with housing 11 and thus difficulties often associated with cords and cables is avoided.

By way of further advantage, the use of offset light pipes 32 and 33 provide virtually shadowless illumination due to overlapping offset light sources. By way of additional advantages, the detented attachment described below in greater detail of mirror support 15 to housing 11 permits the use of a variety of mirror supports for flexible imaging as well as the extension of supported mirrors to a variety of distances from the imaging lens. Because threaded coupler 40 is threaded to receive conventional mirror supports, additional costs of custom mirror pieces is avoided. Thus, the present invention structure exhibits numerous advantages over the above-described prior art structures.

FIG. 2 sets forth a section view of the present invention dental camera system taken along section lines 2—2 in FIG. 1. Camera system 10 includes a generally cylindrical housing 11 which defines an interior cavity 17. Housing 11 further defines a camera passage 29 which receives camera 20 in a precision fit. Housing 11 further defines an elongated passage 61 extending rearwardly from aperture 34 of front face 26 (seen in FIG. 1). As is better seen in FIG. 3, housing 11 further supports a pair of spring biased detent balls 70 and 71. In accordance with an important aspect of the present invention, an elongated extension shaft 62 is received within passage 61 of housing 11 and defines a plurality of spaced detent grooves 63, 64, 65 and 66. Extension shaft 62 is secured to threaded coupler 40 which in turn supports mirror shaft 41, mirror attachment 43 and mirror 42 in the manner described above. In the position shown in FIG. 2 and as is better seen in FIG. 3, detent ball 70 is received within detent groove 66 of extension shaft 62 to maintain the position of extension shaft 62 to that shown in FIG. 2. By similar construction to that shown in FIG. 3 for detent ball 70, detent ball 71 is received within detent groove 65 of extension shaft 62 to further secure shaft 62 within passage 61. In the event greater extension of mirror shaft 41 is desired, threaded coupler 40 and mirror shaft 41 may be drawn outwardly from housing 11 in the direction indicated by arrow 16 with sufficient force to overcome the retaining force of detent balls 70 and 71 and withdraw extension shaft 62 outwardly from passage 61. As shaft 62 continues to be withdrawn, an extension is reached in which detent ball 70 extends into detent groove 65 and detent ball 71 extends into detent groove 64. At this point, mirror support 15 is once secured within housing 11 but is extended outwardly one incremental distance. In further accordance with the present invention, mirror support 15 may be further withdrawn until detent grooves 64 and 63 are aligned with detent balls 70 and 71 respectively to lock mirror support 15 in a further extended position.

As described above, focus sleeve 25 is secured to focus ring 35 of camera 20 by a plurality of set screws 53. To facilitate the coupling between the plurality of set screws coupling focus sleeve 25 to focus ring 35, a corresponding plurality of shallow recesses such as recess 57 are formed within focus ring 35. Similarly, the above-described attachment of housing 11 to collar 36 of camera 20 is provided by a plurality of set screws such as set screws 45 and 46 (seen in FIG. 1) and a corresponding plurality of shallow recesses in collar 36 such as recess 58 shown in FIG. 2. A grommet 60 is received within split caps 50 and 51 and encircles cable sheath 47 to provide a secure seal about cable sheath 47 and protect the interior of housing 11.

FIG. 3 sets forth a partially sectioned front view of camera system 10. Camera system 10 includes a cylindrical housing 11 defining a pair of angled facets 13 and 14 and a cylindrical passage 29. Housing 11 further defines a front face 26 which in turn defines a pair of apertures 30 and 31. A miniature video camera 20 fabricated in the manner described above is received within camera passage 29 and secured in the above-described manner. Camera 20 includes a front lens 22 and a surrounding lens ring 23. A pair of fiber-optic bundle light pipes 32 and 33 extend through apertures 30 and 31 in housing 11 respectively. Housing 11 further defines a generally cylindrical passage 61 which receives an extension shaft 62. As described above, extension shaft 62 supports mirror support 15 and defines a plurality of detent grooves 63 through 66. Housing 11 further defines a detent recess 73 which supports a spherical detent ball 70 and a detent spring 72. Detent recess 73, spring 72 and detent ball 70 cooperate to form a conventional detent mechanism which urges detent ball 70 toward extension shaft 62 to provide a detent mechanism for securing the position of extension shaft 62 in accordance with the location of grooves 63 through 66. As mentioned above, housing 11 supports a second detent mechanism substantially identical to that shown in FIG. 3.

FIG. 4 sets forth a rear view of camera system 10. Camera system 10 includes a cylindrical housing 11 and a end cap 12 supported thereon. As described above, end cap 12 comprises a pair of oppositely facing C-shaped split caps 50 and 51. A grommet 60 is supported between split caps 50 and 51 and encircles a cable sheath 47 which extends outwardly through grommet 60. A cable 48 constructed in accordance with conventional fabrication techniques is coupled to camera 20 and extends outwardly through cable sheath 47. A pair of fiber-optic light pipes 32 and 33 are received within cable sheath 47 and are coupled to a conventional source of illumination (not shown). Split cap 51 defines a pair of apertures 80 and 81 which receive a pair of fasteners 90 and 91. Fasteners 90 and 91 are threadably received within the end portion of housing 11 to secure split cap 51 to housing 11. Similarly, split cap 50 defines a pair of apertures 82 and 83 which receive threaded fasteners 92 and 93 respectively to provide a threaded attachment of split cap 50 to housing 11.

FIG. 5 sets forth a section view of the present invention camera system taken along section lines 5—5 in FIG. 4. Camera system 10 includes an elongated cylindrical housing 11 having a pair of split end caps 50 and 51 secured to the rear end thereof. Split caps 50 and 51 support an annular grommet 60 and are secured to housing 11 by a quartet of fasteners 80 through 83 (seen in FIG. 4). Housing 11 further defines a planar front face 26 having a pair of apertures 30 and 31 defined therein. Housing 11 further defines a pair of elongated light pipe channels 85 and 86 extending rearwardly from apertures 30 and 31 respectively. A pair of fiber-optic light pipes 32 and 33 are supported within light pipe guides 85 and 86 respectively and extend rearwardly from apertures 30 and 31 to a common tying member 84. Thereafter, light pipes 32 and 33 extend outwardly through cable sheath 47 and grommet 60. In accordance with conventional fabrication techniques, light pipes 32 and 33 are coupled to an external source of illumination (not shown). When energized with a conventional source of illumination, light pipes 132 and 33 produce a pair of outwardly extending dispersing light beams 94 and 95. Light beams 94 and 95 form generally conical expanding light beams having interior angles 74 and 75 sufficiently large to cause overlapping of light beams 94 and 95. While the angle of dispersion of light beams 94 and 95 may be varied in accordance with design choice, it has been found advantageous to use approximately 68 degrees angles of dispersion for angles 74 and 75. When so selected, the offset position of light pipes 32 and 33 cooperates with the angular dispersion of light beams 94 and 95 to provide bidirection illumination of the to-be-imaged object thereby virtually eliminating shadows. Miniature video camera 20 is shown in dashed line outline representation in FIG. 5 to permit the details of light pipes 32 and 33 and light pipe guides 85 and 86 to be shown.

What has been shown is a convenient, low cost and easy to use dental camera system which maximizes the capabilities and flexibilities of the miniature video camera. The system shown provides substantial advantage in that the imaging mirror distance from the camera lens may be varied in accordance with the particular use. In addition, the housing of the present invention system is fabricated to provide easy access to both the focusing and aperture adjusting controls of the video camera. Overall size is maintained at a slightly larger diameter cylindrical configuration to provide easy handling and manipulation by the practitioner. In addition, the camera is readily removable from the housing without the need of disturbing the miniature video camera and its cable system. Thus no change or operation is performed upon the camera which would interfere with or affect its manufacture's warranty.

While particular embodiments of the invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention.

What is claimed is:

1. For use in imaging a portion of the mouth and teeth of a patient, a dental camera system comprising:

a video camera defining an elongated generally cylindrical shape and having a frontal lens, an aperture adjustment ring, a focus adjustment ring and a connecting cable;

a housing defining a generally cylindrical shape and having an interior passage configured to receive said camera such that said aperture adjustment ring and focus adjustment ring are exposed;

a pair of light sources positioned in an offset array adjacent said frontal lens;

a mirror support coupled to said housing and adjustably extending thereupon; and a mirror secured to said mirror support.

2. A dental camera system as set forth in claim 1 wherein said housing defines an elongated notch for exposing said focus and aperture adjustment rings.

3. A dental camera system as set forth in claim 2 further including a cylindrical sleeve received upon said focus adjustment ring.

4. A dental camera as set forth in claim 3 wherein said housing defines an interior mirror support passage beneath said camera and wherein said mirror support includes an elongated shaft extending into said mirror support passage in a slidable attachment.

5. A dental camera system as set forth in claim 4 wherein said housing includes a detent mechanism communicating with said detent passage and wherein said elongated shaft defines a plurality of spaced detent grooves for being engaged by said detent mechanism.

6. A dental camera system as set forth in claim 5 wherein said housing defines a front face and a pair of offset apertures and wherein said pair of light sources include a pair of fiber-optic light pipes having output ends within said offset apertures and extending through said housing for coupling to a remote source of light.

7. A dental camera system as set forth in claim 6 wherein said mirror support includes a mirror shaft attached to said mirror and a threaded coupling for removable attachment of said mirror shaft to said elongated shaft.

8. A dental camera system as set forth in claim 7 wherein said housing defines a housing end and includes an end cap having a pair of opposed c-shaped split cap portions and means for securing said split caps to said housing end.

9. A dental camera system as set forth in claim 8 wherein said elongated notch includes a pair of longitudinally extending angled facets extending outwardly from said camera.

10. A dental camera system as set forth in claim 9 wherein said housing defines a pair of light pipe guides for supporting portions of said light pipes adjacent said camera.

11. For use in supporting an elongated generally cylindrical video camera, a dental camera system comprising:

an elongated generally cylindrical housing defining a camera passage for receiving a camera, a front face, a rear face, a notch extending from said front face exposing a portion of said camera passage;

a mirror removably attachable to said housing; and a pair of light sources directed outwardly from said front face.

12. A dental camera system as set forth in claim 11 wherein said housing and said camera passage define respective major axes which are offset by a predetermined distance.

13. A dental camera system as set forth in claim 12 wherein said front face defines a pair of offset apertures and wherein said light sources include fiber-optic light pipes having output ends within said offset apertures.

* * * * *